United States Patent
Friedman et al.

(10) Patent No.: US 7,620,458 B2
(45) Date of Patent: Nov. 17, 2009

(54) SHEATH AND ELECTRICAL LEAD

(75) Inventors: Paul A. Friedman, Rochester, MN (US); Charles J. Bruce, Rochester, MN (US); Samuel J. Asirvatham, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 614 days.

(21) Appl. No.: 11/075,513

(22) Filed: Mar. 8, 2005

(65) Prior Publication Data

US 2005/0209668 A1 Sep. 22, 2005

Related U.S. Application Data

(60) Provisional application No. 60/551,639, filed on Mar. 9, 2004.

(51) Int. Cl.
*A61N 1/00* (2006.01)
(52) U.S. Cl. .................................. 607/122; 600/374
(58) Field of Classification Search ......... 600/372–393; 607/115–156
See application file for complete search history.

(56) References Cited

U.S. PATENT DOCUMENTS 5,087,243 A * 2/1992 Avitall .......................... 604/20
5,871,532 A * 2/1999 Schroeppel .................. 607/128
5,904,711 A * 5/1999 Flom et al. ................... 607/129
6,223,079 B1 4/2001 Bakels et al.
2004/0215301 A1* 10/2004 Lokhoff et al. .............. 607/116

OTHER PUBLICATIONS

Abraham, "Cardiac resynchronization therapy for heart failure: biventricular pacing and beyond," *Curr. Opin. Cardiol.*, 2002, 17(4):346-352.
Abraham et al., "Cardiac Resynchronization in Chronic Heart Failure," *N. Engl. J. Med.*, 2002, 346(24):1845-1853.
Brugada et al., "Nonsurgical Transthoracic Epicardial Radiofrequency Ablation," *J. Am. Coll. Cardiol.*, 2003, 41(11):2036-2043.
Pappone et al., "Cardiac Contractility Modulation by Electric Currents Applied During the Refractory Period in Patients with Heart Failure Secondary to Ischemic or Idiopathic Dilated Cardiomyopathy," *Am. J. Cardiol.*, 2002, 90(12):1307-1313.
Schweikert et al., "Percutaneous Pericardial Instrumentation for Endo-Epicardial Mapping of Previously Failed Ablations," *Circulation*, 2003, 108:1329-1335.
Sosa et al., "A New Technique to Perform Epicardial Mapping in the Electrophysiology Laboratory," *J. Cardiovasc. Electrophysiol.*, 1996, 7:531-536.
Stevenson and Soejima, "Inside or Out? Another Option for Incessant Ventricular Tachycardia," *J. Am. Coll. Cardiol.*, 2003, 41(11):2044-2045.

* cited by examiner

*Primary Examiner*—Scott M Getzow
(74) *Attorney, Agent, or Firm*—Fish & Richardson P.C.

(57) ABSTRACT

The invention describes a steerable sheath for percutaneous epicardial access. The invention also describes a novel lead to facilitate left ventricular pacing and efficient defibrillation.

10 Claims, 8 Drawing Sheets

SHEATH AND ELECTRICAL LEAD

CROSS REFERENCE TO RELATED APPLICATIONS

This application claims the benefit of priority under 35 U.S.C. §119(e) to U.S. application Ser. No. 60/551,639 filed Mar. 9, 2004.

TECHNICAL FIELD

This invention relates to a novel sheath and electrical lead, and more particularly to a sheath in which the distal portion is angled and/or steerable for optimal placement against the epicardium via percutaneous epicardial access, and an electrical lead for defibrillation and/or pacing at the epicardium.

BACKGROUND

A percutaneous, transvenous, endocardial approach has become standard practice for catheter ablation of several types of arrhythmias and pacemaker lead implantation. However, this approach has limitations, including the inability to access intramural or epicardial portions of arrhythmia circuits or inability to gain access to desirable tributaries of the coronary venous system. Technological improvements such as cooled-tip or larger-tip ablation catheters and different energy sources for tissue ablation have not completely solved the problem.

Before the advent of percutaneous catheter-based endocardial ablation methods, surgical epicardial approaches were used for treatment of refractory arrhythmias, particularly ventricular tachycardia (VT) and supraventricular tachycardia (SVT), by using an accessory pathway. Epicardial ablation has been achieved through various methods, including open-chest surgery, thoracoscopy, and by way of epicardial vessels such as the coronary sinus. However, despite the development of catheter-based, endocardial ablation techniques, some arrhythmia substrates might not be accessible from the endocardium. For example, VT from ischemic cardiomyopathy might have significant portions of the arrhythmia circuit in the epicardium. More recently, the percutaneous approach for epicardial mapping and ablation of VT has been shown to be feasible, primarily in patients with ischemic cardiomyopathy.

Currently, epicardial pacing is often required in small children, in patients with residual right-to-left shunts, and in patients with chambers that cannot be accessed by the transvenous route. Although endocardial pacing requires less extensive surgery than does epicardial lead implantation, there is concern about vascular obstruction, AV valve integrity, and the limitations of lead accommodation during growth with epicardial pacing. The risks have generally been outweighed by the higher acute and chronic stimulation thresholds of conventional epicardial leads, resulting in premature battery depletion and the need for subsequent operations. Recent advances in epicardial leads and surgical approaches have demonstrated improved early pacing and sensing thresholds. Prior studies evaluating epicardial leads in children have had low patient numbers or have involved series that predated both the introduction of lithium iodide batteries and steroid-eluting leads.

Therefore, a steerable sheath delivery system for percutaneous epicarcial access and a permanent lead for pacing and/or defibrillating epicardially is provided by the present invention.

SUMMARY

The invention describes a steerable sheath for percutaneous epicardial access. The invention also describes a novel lead to facilitate pacing and efficient defibrillation, particularly epicardial pacing and defibrillation.

In one aspect, the invention provides a sheath including an elongate enclosure with at least one lumen. A sheath of the invention generally has a proximal and a distal portion defining a longitudinal axis. The distal portion of a sheath of the invention usually includes a tip region that forms an angle with respect to the longitudinal axis of the sheath. The angle of the tip region is typically selected such that when the sheath is inserted into pericardium, the tip region of the sheath is adjacent to epicardium.

In one embodiment, the angle of the tip region is about 90°. In other embodiments, the tip region also can include an electrode ring and/or an ultrasound probe.

In another aspect, the invention provides a steerable sheath that includes a sheath having an elongate enclosure with at least one lumen having a proximal and distal portion that defines a longitudinal axis; and at least one sheath control mechanism for steerably operating the distal portion of the sheath. In one embodiment, the sheath control mechanism includes at least one control arm that extends from the sheath control mechanism to the distal portion of the sheath and is substantially parallel to the longitudinal axis of the sheath.

In certain embodiments, a sheath of the invention also can include at least one monitoring device or sensing element. Representative monitoring devices can include an intracardiac echo or an ultrasound probe device attached to the sheath. A representative sensing element can include one or more electrodes.

In another aspect, the invention provides an apparatus including a sheath that has an elongate enclosure with at least one lumen, and a handle capable of releasable attachment to the proximal portion of the sheath. A sheath of the invention generally has a proximal and distal portion that defines a longitudinal axis, and the distal portion usually includes a tip region. A handle typically includes a sheath control mechanism that engages the sheath to permit positioning of the tip region thereof.

In one embodiment, a sheath control mechanism can include a rotatable steering element that is substantially normal to the longitudinal axis of the sheath. In certain embodiments, the sheath control mechanism includes a control arm engaging element and a steering element. Typically, a control arm engaging element and a steering element are substantially normal to the longitudinal axis of the handle. For example, a sheath can include one or more control arms that each have an engagement flange for engaging the control arm engagement element. A control arm engagement element can include one or more female engagement regions to releasably engage an engagement flange of the control arm.

In another embodiment, the angle of the tip region of the sheath is substantially normal to the longitudinal axis of the sheath (e.g., the angle of the tip region is 90° with respect to the longitudinal axis of the sheath). In certain embodiments, the tip region can include an electrode ring or an ultrasound probe.

In still another aspect, the invention provides an apparatus including a sheath, a handle capable of releasable attachment to the proximal portion of the sheath, and at least one diagnostic or therapeutic lead. The sheath generally includes an elongate enclosure with at least one lumen having a proximal and distal portion that defines a longitudinal axis. The distal portion of a sheath of the invention generally includes a tip region. Typically, the handle includes a sheath control mechanism to engage the sheath to permit positioning of the tip region thereof. The diagnostic or therapeutic lead(s) usually have a size suitable for positioning in the lumen of the sheath.

In yet another aspect, the invention provides methods for percutaneous placement of an epicardial lead or other therapeutic or monitoring device. Such a method can include providing a sheath of the invention; inserting the distal portion of the sheath into pericardium; positioning the tip region adjacent to epicardium; and inserting at least one diagnostic or therapeutic lead into the lumen. A sheath used in the methods of the invention generally includes an elongate enclosure with at least one lumen having a proximal and distal portion that defines a longitudinal axis; and a handle capable of attachment to the proximal portion of the sheath and having a sheath control mechanism. Typically, the distal portion of the sheath includes a tip region substantially normal to the longitudinal axis such that the sheath control mechanism can engage the sheath to permit positioning of the tip region thereof.

In an embodiment of the method, the lead can be permanently positioned in the epicardium. In another embodiment, a sheath used in the above-described methods further includes an electrode ring. Using such a sheath, a method of the invention also can include assessing myocardial electrical activity prior to inserting the diagnostic or therapeutic lead into the lumen. In yet another embodiment, a sheath used in the above-described methods can further include an ultrasound probe. Using such a sheath, a method of the invention also can include visualizing tissues and/or vessels prior to inserting the diagnostic or therapeutic lead into the lumen.

In still another aspect, the invention can include methods for percutaneous placement of an epicardial lead or other therapeutic or monitoring device. Such a method can include providing a sheath of the invention; inserting the distal portion of the sheath into pericardium; positioning the tip region adjacent to epicardium; inserting at least one diagnostic or therapeutic lead into the lumen; and removing the handle such that at least one of the sheath or the lead remain in the pericardium. As described above, a sheath for use in the methods of the invention can include an elongate enclosure with at least one lumen having a proximal and distal portion that defines a longitudinal axis; and a handle releasably attached to the proximal portion of the sheath that includes a sheath control mechanism. Generally, the distal portion of the sheath includes a tip region substantially normal to the longitudinal axis of the sheath, which allows the sheath control mechanism to engage the sheath and permit positioning of the tip region thereof.

In another aspect, the invention provides a kit for percutaneous placement of an epicardial lead. A kit of the invention can include a sheath and at least one diagnostic or therapeutic lead. Generally, a sheath of the invention includes an elongate enclosure with at least one lumen having a proximal portion and a distal portion that defines a longitudinal axis and a handle capable of releasable attachment to the proximal portion of the sheath and having a sheath control mechanism. Generally, the distal portion of a sheath of the invention includes a tip region, such that the sheath control mechanism can engage the sheath to permit positioning of the tip region thereof.

In some embodiments of the above-described sheath, the elongate enclosure also can have an access port. An access port can be used in the methods of the invention to remove the sheath such that the lead remains in the pericardium or to remove the lead and the handle such that the sheath remains in the pericardium.

In still another aspect, the invention provides a deployable lead comprising at least one arm, the arm having a distal end and a hinged end, wherein the arm comprises at least one electrode. Typically, the hinged end of the arms is attached to a longitudinal body of a diagnostic or therapeutic lead. In different embodiments of the invention, the electrodes can be attached to the arms at the distal end of the arms, or can be attached to the arms at a position medial to the distal end and the hinged end of the arm. Generally, the distal ends of the arms move through an angle α relative to the longitudinal axis of the diagnostic or therapeutic lead, for example, between about 0° and about 90° or between about 0° and about 180° relative to the longitudinal axis of the diagnostic or therapeutic lead.

In another embodiment, the arm also can include a membranous material. In certain embodiments, the material can attached to a second arm, and/or can be attached to a longitudinal body of a diagnostic or therapeutic lead. In some embodiments, the material is conductive (e.g., the material can further include electrodes).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION

Recent advances in cardiology have resulted in an enhanced ability to place cardiac pacing and other leads in non-traditional locations, such as in the vicinity of the left ventricle. Due to the risk of thromboembolism, intra-cavitary left-ventricular lead placement is generally avoided. The recent introduction of biventricular pacing and its documented success in multiple randomized, prospective clinical trials has led to great interest in placement of permanent leads capable of left ventricular pacing. While biventricular leads were initially placed epicardially, due to the need for thoracotomy (and its attendant risk and prolonged recovery), coronary sinus venous access has been adopted as the primary means of lead placement. Leads designed to pace the left ventricle are threaded through the coronary veins to epicardial venous positions. However, due to the variability of human anatomy and technical limitations with this approach, as many as 8-12% of patients in prospective trials have been unable to receive this form of therapy. Clearly, a new method of rapidly delivering leads to the left ventricle would be of great utility in the therapy of the 5 million patients in the U.S. with heart failure. This invention describes such a technology.

Additionally, this invention describes a novel lead, capable of left ventricular pacing and defibrillation with very low defibrillation thresholds. Such a lead may permit widespread applicability of left ventricular pacing, which may be as effective as biventricular pacing, and defibrillation with a single lead. Importantly, biventricular pacing is facilitated and improved by the capability of selecting from multiple pacing sites within a single lead. Furthermore, enhanced defibrillation efficacy by means of this novel lead may result in greater longevity of smaller implantable defibrillators. If defibrillation effectiveness is sufficient to eliminate the need for defibrillation threshold testing, a broader array of health care providers such as general cardiologists or general surgeons could perform implantation, thereby facilitating wider adoption of this therapy. Additionally, the introduction of painless defibrillation shocks by means of autonomic nervous stimulation may be possible, as autonomic and pain fibers are epicardially located.

Sheath

Figure 1:
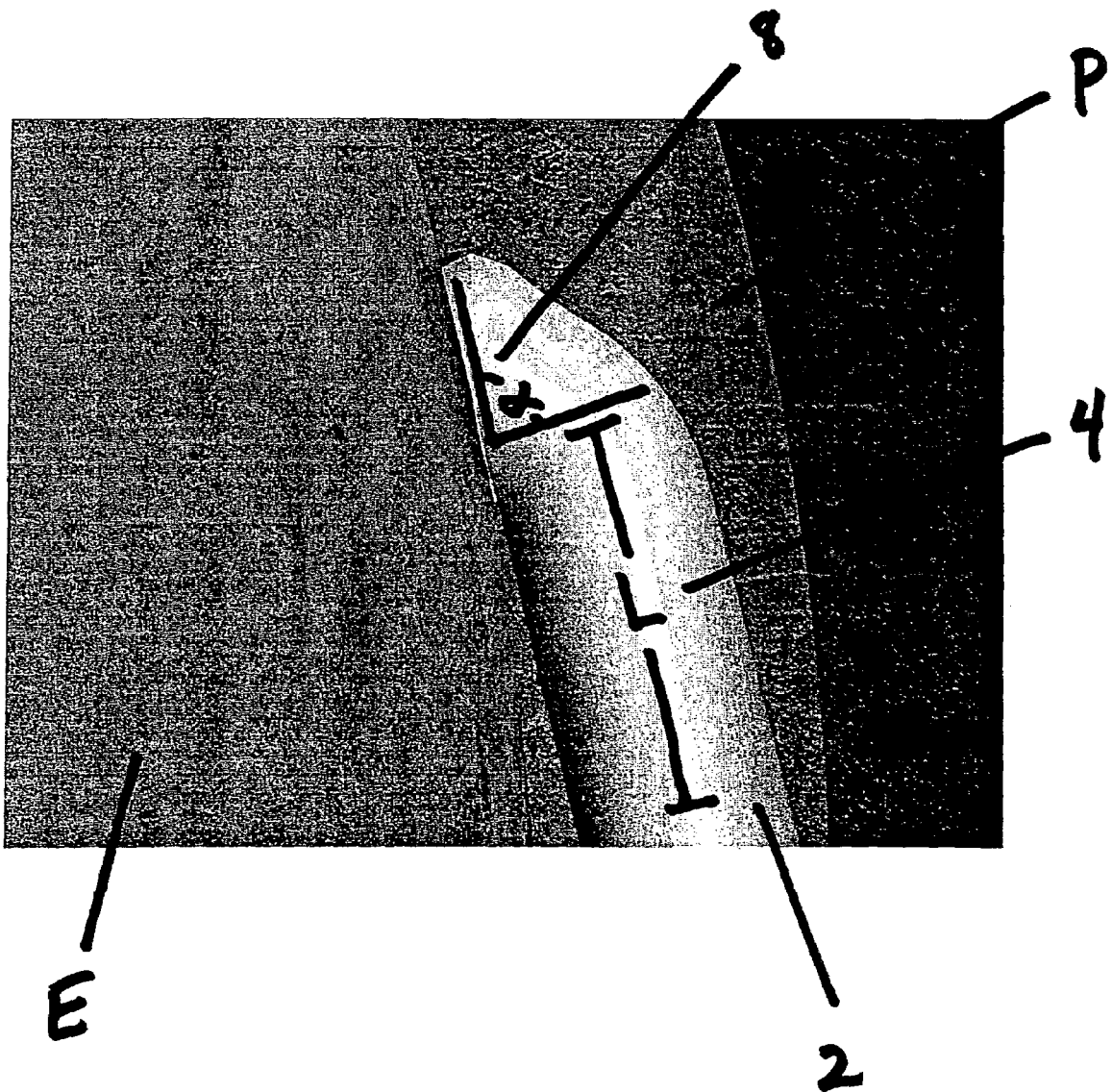
FIG. 1 is a photograph of the distal portion of a sheath of the invention in which the tip is perpendicular to epicardium.

FIG. 1 shows a distal 4 portion and tip region 8 of a sheath 2 of the invention approximated against the epicardium E. The tip region 8 of the sheath 2 has a curved shape so as to position a lead or ablation electrode within the pericardium P perpendicular to the surface of the epicardium E. The angle α of the tip region 8 is relative to the longitudinal axis L of the sheath 2. In some embodiments, the angle α of the tip region 8 is substantially normal to the longitudinal axis L of the sheath 2. FIG. 1 shows an angle α at the tip region 8 of about 90°. The curved shape at the tip region of a sheath of the invention can facilitate flush contact with and active fixation of a lead or ablation electrode onto the epicardium E.

Figure 2:
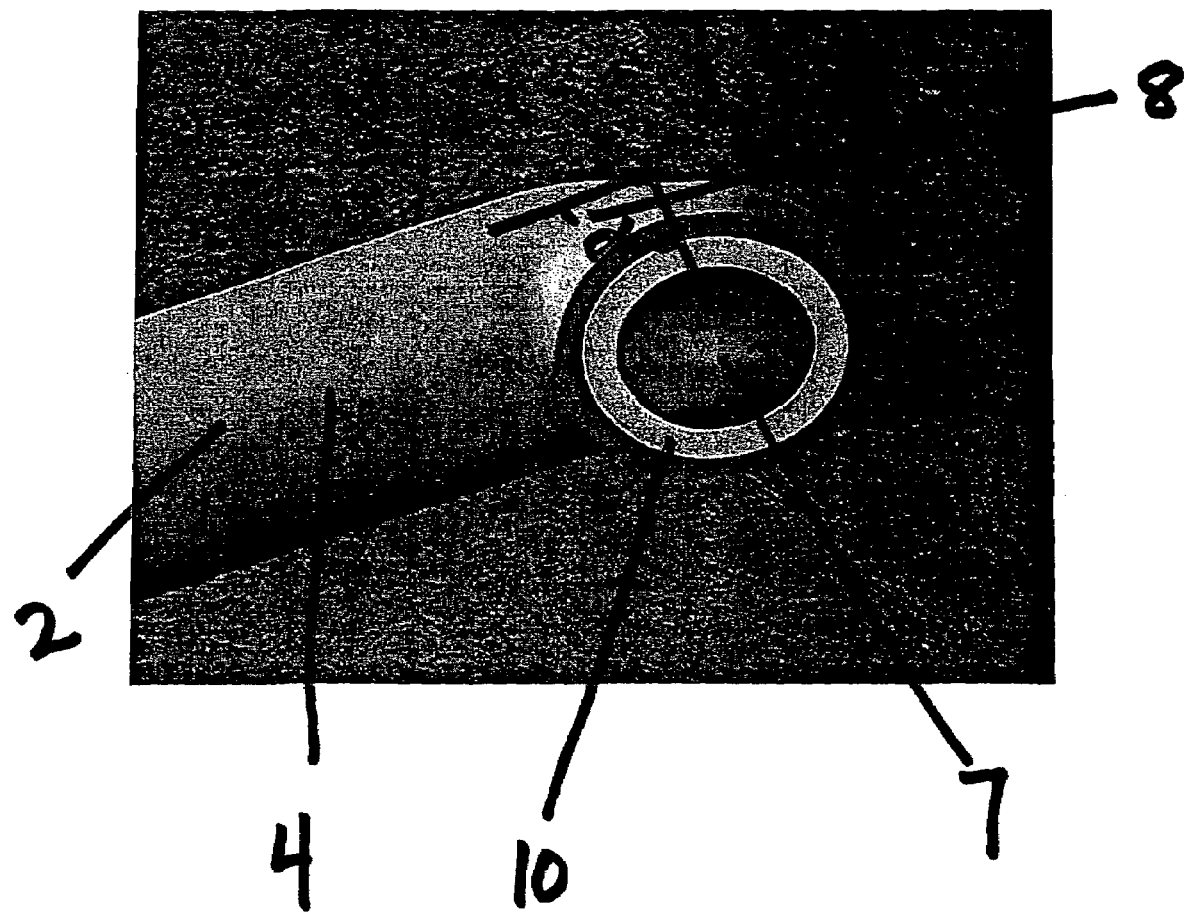
FIG. 2 is a photograph of a ring electrode at the distal portion of the sheath to permit electrical tissue assessment before lead deployment.

FIG. 2 shows the distal 4 portion of a sheath 2 of the invention, including the lumen 7 of the sheath. FIG. 2 shows an embodiment in which an electrode ring 10 at the tip region 8 of a sheath 2 permits pacing to assess myocardial viability and phrenic capture at multiple sites prior to lead fixation, further facilitating lead placement. In addition, an ultrasound probe can be integrated into a sheath of the invention. Ultrasound imaging permits imaging of tissues and epicardial vessels as the sheath passes over the epicardium prior to lead fixation. In some embodiments, the sheath can have more than one lumen to permit placement of more than one sensing element or monitoring device.

Figure 3:
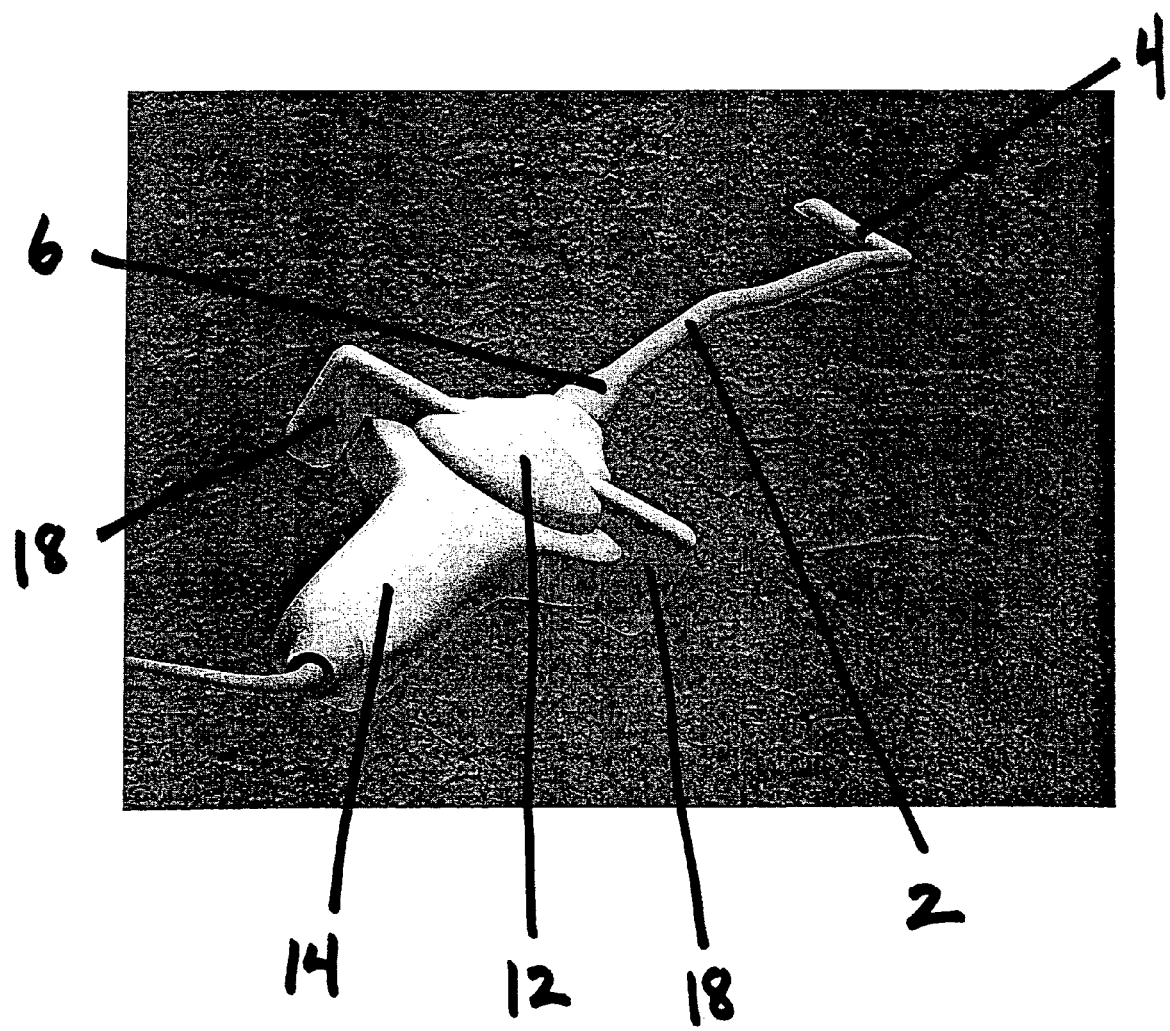
FIG. 3 is a photograph of a sheath of the invention having a steering mechanism at the distal portion.

The invention further includes a steerable sheath as shown in FIG. 3. FIG. 3 shows an elongated sheath 2 having a proximal 6 and distal 4 portion that defines a longitudinal axis L. The embodiment of the steerable sheath shown in FIG. 3 also has a sheath control mechanism 12 for steerably operating the distal 4 portion of the sheath 2. The sheath control mechanism 12 shown in FIG. 3 includes a steering element 18 that can be at least partially rotated clockwise and counter-clockwise, which actuates internal wires extending down the longitudinal axis of a sheath of the invention.

Many types of control mechanisms for steering the distal portion of a sheath are suitable for use in the present invention. In the embodiment shown in FIG. 3, the sheath control mechanism 12 can include at least one control arm 16 (not visible) that extends from the sheath control mechanism 12 to the distal 4 portion of the sheath and is substantially parallel to the longitudinal axis L of the sheath 2. Clockwise or counterclockwise rotation of the steering element 18 results in movement of the distal 4 portion of the sheath via the control arm 16.

A steerable sheath of the invention can be deployed percutaneously utilizing known techniques (see, for example, Sosa et al., 1996, *J. Cardiovasc. Electrophysiol.*, 7:531-6). Access to the pericardium has been well described and methods are well known to those of skill in the art. A steerable sheath as described herein can be used for manipulating and affixing temporary or permanent leads for pacing, defibrillation, ablation, or other diagnostic or therapeutic uses in the epicardium.

Figure 4:
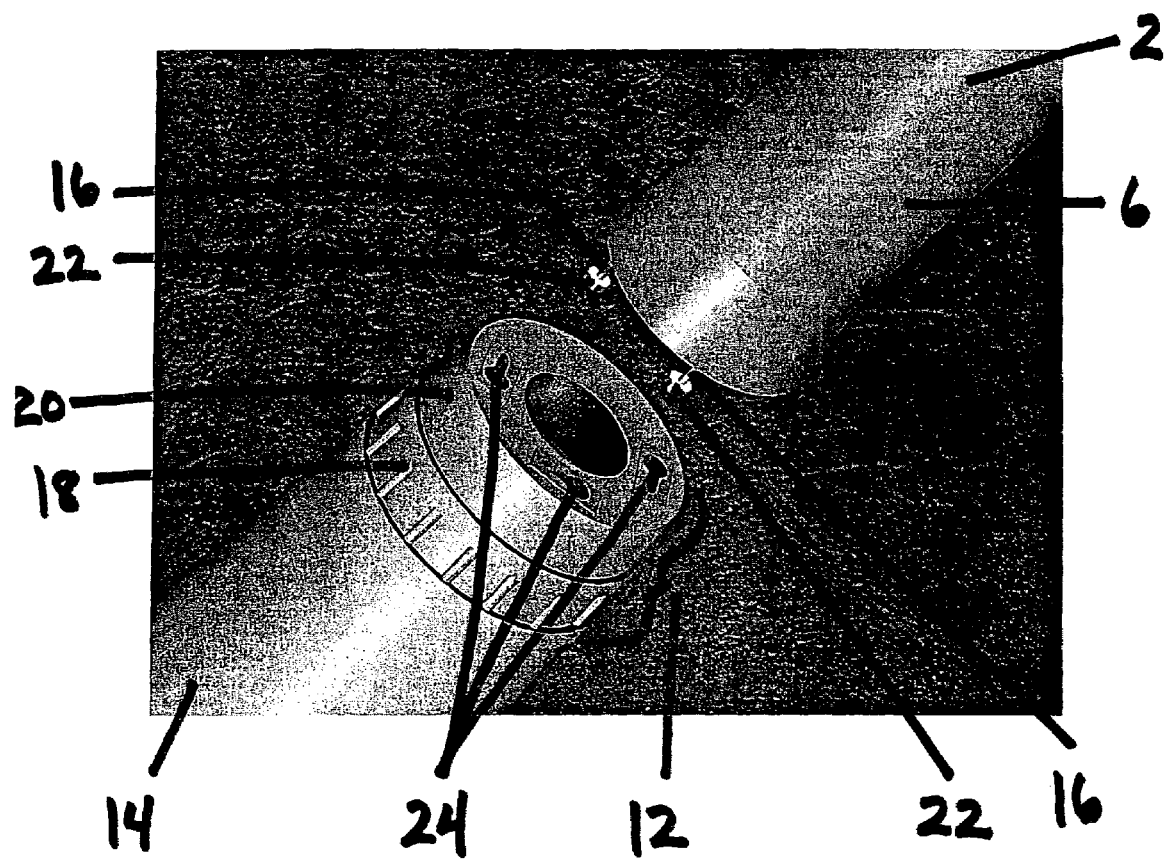
FIG. 4 is a photograph showing an embodiment in which a sheath of the invention is detachable from a handle. The metal projections are pull levers for steering the distal portion of the sheath.

FIG. 4 shows an embodiment of a sheath apparatus in which the handle 14 is detachable from the proximal 6 portion of the sheath 2. FIG. 4 shows the proximal 6 portion of an elongated sheath and the distal portion of a handle 14. A detachable handle 14 in an apparatus of the invention will include a sheath control mechanism 12, which is able to detachably engage the proximal 6 portion of a sheath 2 to permit positioning of the distal 4 portion and the tip region 8 of the sheath 2 adjacent to epicardium E. In embodiments in which the handle is detached, the proximal portion of the sheath can be sutured in place to provide greater lead stability.

In one embodiment, a sheath control mechanism 12 can include a rotatable steering element 18 such as that shown in FIG. 1. In some embodiments in which the longitudinal axis L of the sheath 2 is in a relaxed position (i.e., not being steered), such a rotatable steering element 18 is generally substantially normal to the longitudinal axis L of the sheath 2.

In another embodiment such as the embodiment shown in FIG. 4, a sheath control mechanism 12 can include a control arm engagement element 20 and a rotatable steering element 18. In the embodiment shown in FIG. 4, the control arm engagement element 20 and the rotatable steering element 18 are substantially normal to a longitudinal axis L of the handle 14.

In the embodiment shown in FIG. 4, the sheath 2 includes one or more control arms 16 that each can have an engagement flange 22 for engaging the control arm engagement element 20 on the handle 14. The control arm engagement element 20 shown in FIG. 4 contains one or more female engagement elements 24 to releasably engage an engagement flange 22 of a control arm 16. Although not necessary, it may be desirable to have control arms 16 that are low profile so that the control arms 16 do not protrude from the sheath after the handle is removed. Low profile control arms would be advantageous in cases in which the sheath is to be left permanently in place.

Generally, two or more control arms are used to maneuver a steerable sheath of the invention. FIG. 4 shows three control arms 16 and three corresponding female engagement elements 24. In other embodiments, an electrical lead can be positioned along the longitudinal axis L of a sheath 2 in a similar manner as a control arm 16. The electrical lead can connect to a removable handle 14 via female engagement elements 24.

In an embodiment, the tip region of the sheath in an apparatus of the invention can include an electrode ring 10, such as that shown in FIG. 2, or an ultrasound probe or a fiberoptic light source and window (not shown).

In another embodiment of an apparatus of the invention, a peel-away sheath can be used with a removable handle. Peel-away sheaths are well known in the art and are usually opened by slitting or tearing at a perforation in the sheath. A peel-away sheath can still accommodate an electrode ring at the tip region of a sheath for initial pacing. Such an electrode ring can be discontinuous, or it can be weakened at a position corresponding to the position in the sheath that is opened.

The invention also provides a kit for percutaneous placement of an epicardial lead. Such a kit can include a sheath of the invention and at least one diagnostic or therapeutic lead 36 having a size suitable for positioning in the at least one lumen 7 of a sheath of the invention.

Deployable Lead

A deployable lead of the invention can be percutaneously placed to facilitate epicardial left ventricular pacing. Epicardial left ventricular pacing is useful, for example, in biventricular pacing. Such a lead of the invention also can facilitate lower defibrillation thresholds and could be useful for other technologies such as cardiac contraction modulation.

Figure 5:
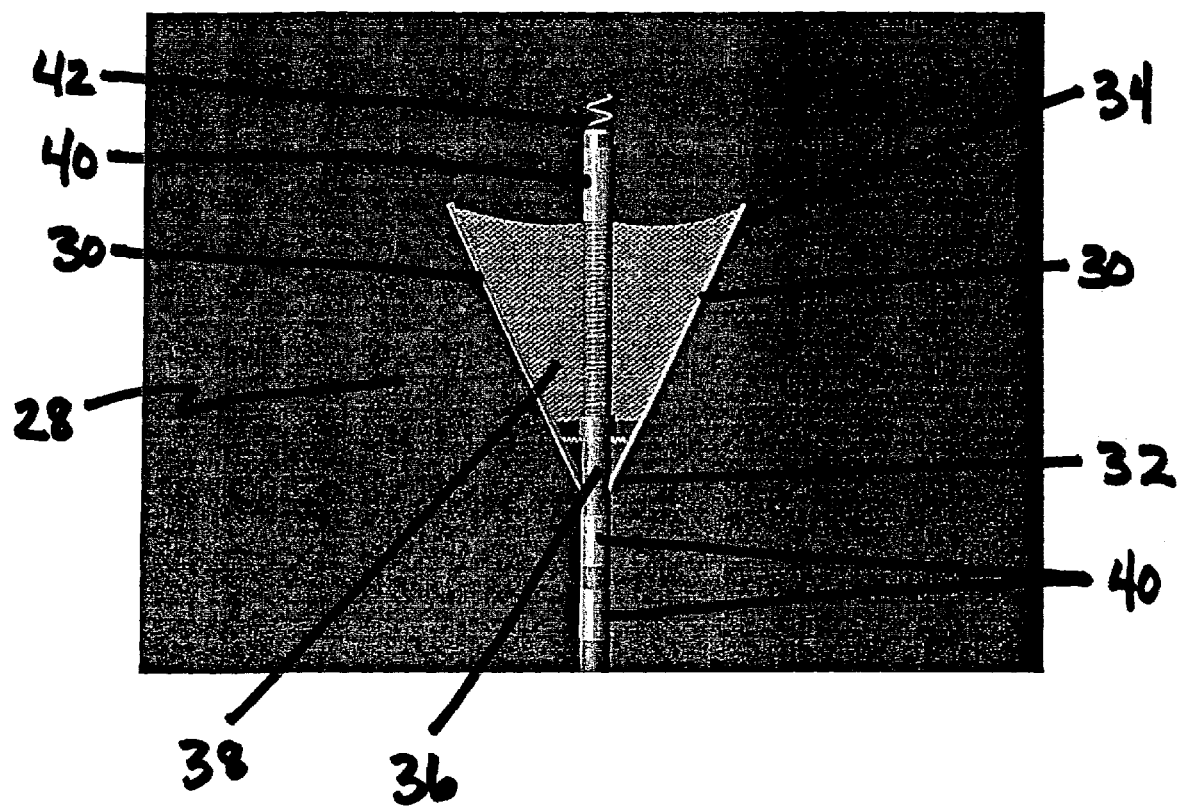
FIG. 5 is a photograph showing a deployed lead of the invention. This embodiment also includes a distal straight screw for epicardial atrial pacing, proximal electrode rings for epicardial ventricular pacing, and mesh material for defibrillation or multi-site pacing.

FIG. 5 shows a deployable lead 28 of the invention. A deployable lead 28 of the invention includes at least one arm 30 having a distal end 34 and a hinged end 32. Usually, the arm(s) 30 of a deployable lead 28 of the invention include at least one electrode. Such electrodes can be attached to the arms 30 at the distal end 34 of the arms 30, or electrodes can be attached to the arms 30 at a position medial to the distal end 34 and the hinged end 32 of the arm 30. In some embodiments, the hinged end 32 of the arms 30 can be attached to a longitudinal body of a diagnostic or therapeutic lead 36.

FIG. 5 shows a deployable lead 28 of the invention containing an optional membranous material 38. Such a material can be used to enlarge the defibrillation surface area provided by the deployable lead. Such a membranous material 38 can be attached to a second arm 30, or can be attached to a longitudinal body of a diagnostic or therapeutic lead 36. In certain embodiments, the membranous material 38 can be conductive to enhance defibrillation and also may contain discrete electrodes for pacing. In certain embodiments, a part or portion of the membranous material 38 can be conductive, while the opposing part or portion of the membranous material 38 can be reflective, to thereby direct the energy. For example, the conductive portion (or discrete electrodes) can be the internal layer of the membranous material 38, while the reflective portion can be the outside layer.

Figure 6:
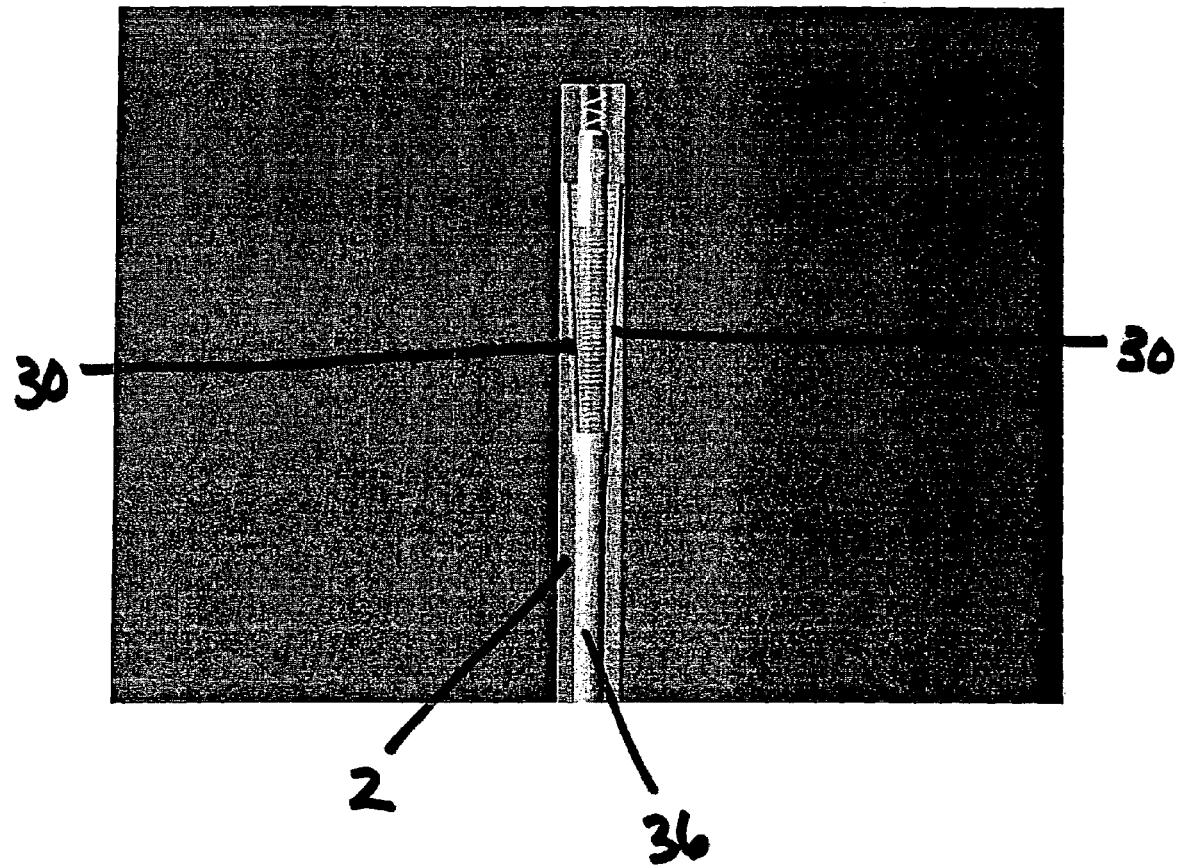
FIG. 6 is a photograph of a lead of the invention in a retracted position in a sheath.

The arms 30 of a deployable lead 28 of the invention are adjacent to the main lead body in the low profile position (FIG. 6). When the sheath is withdrawn, the arms are deployed, thereby moving the distal ends of the arms through an angle α relative to the longitudinal axis of a diagnostic or therapeutic lead 36. For example, the angle α can be between about 0° and about 90° relative to the longitudinal axis of the diagnostic or therapeutic lead 36, or the angle α can be between about 0° and about 180° relative to the longitudinal axis of the diagnostic or therapeutic lead 36. Deployment can be due, for example, to spring action, or by making the arms from materials having shape-memory.

FIG. 6 shows a deployable lead 28 of the invention in a retracted stage. In the embodiment shown in FIG. 6, the diagnostic or therapeutic lead 36 to which the deployable lead is attached can be pulled back into a sheath, thereby retracting the deployable lead of the invention. To move or reposition the arms 30 of a deployable lead 28, the sheath 2 could be advanced over the lead 36, bringing the arms 30 together until a desirable position is found.

In another embodiment, multiple arms 30 that can be deployed to different angles a relative to the longitudinal axis L of the sheath 2 can be used to create a fan-like structure upon deployment. Electrodes on the arms or at unique sites within a membranous material 38 could allow for simultaneous or sequential left ventricular pacing or left ventricular sub-threshold stimulation. The availability of multiple electrodes at different positions along an arm or within a membranous material permits selection of different pacing sites using a single deployed lead. Such selection is useful in the event of a change in threshold at one site, the development of phrenic stimulation with changing body position, or the evaluation of the hemodynamic benefit of pacing at different unipolar or bipolar sites. Additionally, the option of simultaneously or sequentially pacing from multiple sites in a supra- or sub-threshold manner may add additional benefits in the setting of refractory heart failure.

In an alternative embodiment (not shown), the arms 30 can be deployed using, for example, a pull wire or a screw-type mechanism. Such a pull wire or screw mechanism can be at the proximal end 6 of the sheath for manipulation by the user. A pull wire or screw mechanism also can be used to retract the arms. In the retracted position, the arms generally lay parallel to the longitudinal axis L of the sheath 2.

Electrode rings and/or one or more coil electrodes also can be used for ventricular pacing and/or stimulation in the epicardium. Within the pericardial space, ring electrode contact is assured. The embodiment of the deployable lead shown in FIG. 5, which includes electrode rings 40 and a coil electrode 42, can provide dual chamber pacing and active defibrillation from the same lead. The coil electrode 42 shown in FIG. 5 is essentially contiguous with the longitudinal axis L of the sheath 2. In certain embodiments, an electrode (not limited to coil electrodes) projects from the distal portion of the sheath 2 at an angle. For example, an electrode projecting at an angle can be affixed to the outside of the sheath 2 or can be slidably deployed and retracted from a hole in the sheath 2. Such an electrode (retractable or fixed) can include a barb (not shown) to assist in anchoring the electrode to the epicardium.

In another embodiment, a lead can have a sharp distal end that can be protected within the sheath or exposed. Such a lead can be introduced into the coronary sinus in the same manner in which existing leads are introduced. Once in the coronary sinus, the sharp distal lead can be exposed and used to pierce the venous structure to allow the sheath to exit to the epicardium.

Methods for Using a Sheath or Lead of the Invention

Figure 7:
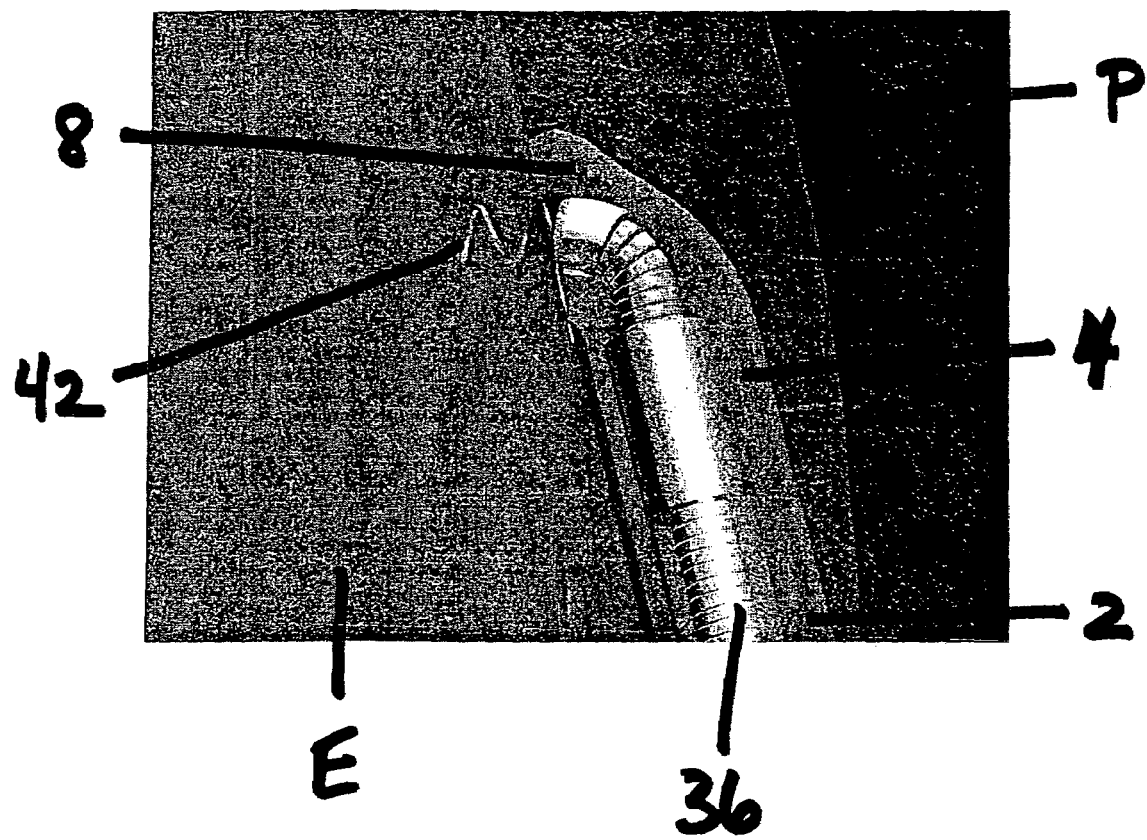
FIG. 7 is a photograph showing an example of how the shape of the distal portion of a sheath of the invention facilitates lead fixation into epicardium.

A steerable sheath of the invention facilitates placement of biventricular pacing leads or ablation catheters. FIG. 7 shows a photograph in which the sheath 2 has been made translucent so as to demonstrate how a diagnostic or therapeutic lead 36 can be introduced into the sheath 2 and positioned adjacent to the epicardium E to allow active fixation of the lead 36. In addition to pacing leads (or wires) and ablation catheters (or electrodes), a steerable sheath of the invention also can be used to deliver, for example, sonomicrometers or (wireless) physiomonitors. A steerable sheath of the invention also can be used for therapeutic injections of, for example, cardiac myocytes.

Generally, a method of the invention can include providing a steerable sheath of the invention, inserting the distal portion of the sheath 2 into pericardium P, positioning the tip region 8 adjacent to epicardium E, and inserting at least one diagnostic or therapeutic lead 36 into the lumen 7 of the sheath 2. In an embodiment, the diagnostic or therapeutic lead 36 can be permanently positioned in the epicardium E. As described above, a steerable sheath of the invention can include a monitoring device or a sensing element such as an electrode ring or an ultrasound probe. In those cases, a method of the invention can further include assessing myocardial electrical activity and/or visualizing tissues and/or vessels. In another embodiment, the method described above can be practiced, followed by removing the handle 14 such that either or both the sheath 2 or the lead 36 remain in the pericardium P.

Figure 8:
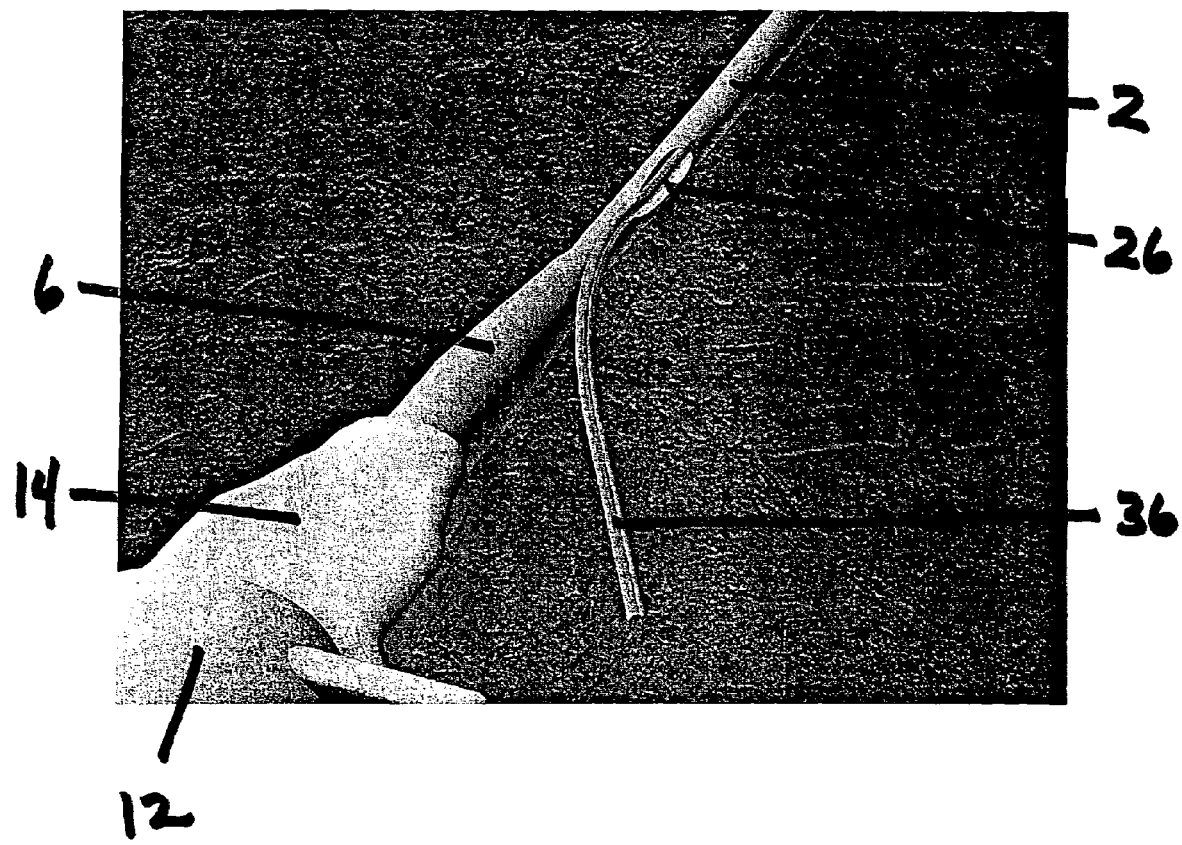
FIG. 8 is a photograph that shows an embodiment of a sheath of the invention with an access port into which a lead can be introduced.

FIG. 8 shows an embodiment in which the sheath 2 has an access port 26 such that the sheath 2 can be removed once a diagnostic or therapeutic lead 36 is introduced. Such an access port 26 in a sheath 2 is contiguous with the lumen 7 of a sheath 2. In certain embodiments of a sheath of the invention, where the sheath 2 has an access port 26, the lead 36 and the handle 14 can be removed, thereby allowing the sheath 2 to remain in the pericardium P as described above. As described above, in the absence of an access port 26, a peel-away sheath can be used.

The embodiment of the sheath shown, for example, in FIG. 8, would be amenable to non-invasive magnetic repositioning. For example, using a magnetic field-type steering device, a lead such as the one shown in FIG. 8 could be actively maneuvered using magnetic guidance. Therefore, the lead can be repositioned without the need for additional invasive intervention. In addition, the presence of a non-magnetic sheath left in place permanently may facilitate magnetic manipulation of leads.

Delivery

The steerable sheath device as described herein can be used for both subxiphoid and medial intercostal transthoracic delivery of a lead. Visceral and parietal pericardial separation is typically widest in the subxiphoid as well as right and left second intercostal space region (site of reflection). In addition, a steerable sheath of the invention can be used for transcoronary venous delivery of a lead, intramyocardial lead delivery, or intracavitary lead placement.

In a transcoronary venous delivery system, the coronary sinus would be cannulated in the usual fashion. However, a Seldinger-type process would be used to puncture the coronary venous system. Anatomically, the sites that would be least likely to result in mediastinal bleeding or arterial damage would be the posterior wall of the great cardiac vein approximately 5-10 mm distal to the posterolateral vein. Entry into the pericardium also can be achieved by piercing the right atrial appendage as is known in the art. Alternatively, a superior puncture in the coronary sinus itself between the first and second atrial veins presents little risk of arterial damage because of the atrial location of the coronary sinus at this site, particularly in the superior or atrial orientation. Once the pericardium is accessed through this site, lead manipulation can be directed in a more ventricular fashion. If pericardial effusion is found to be prohibitive, a modification of the delivery system using a flanged or other closure device can be used to minimize ooze from the venous system.

For intramyocardial lead delivery, intramyocardial puncture from the right ventricular septum can be performed and, for example, using an embodiment of the lead such as that shown in FIG. 8, the lead can be placed in a mid-myocardial septal location. This location may help shorten the QRS duration and synchrony of ventricular contraction. The mid and distal portions of the ventricular septum exhibit considerable anisotropy with right ventricular fibers following the course of the acute marginal arteries and the left ventricular septal fibers following the course of the septal perforators more deeply and the left anterior descending artery more superficially. Thus, an intramyocardial location of a lead in this portion of the septum is unlikely to produce significant QRS shortening. However, a lead placed in this fashion inferior to the membranous interventricular septum (below the bundle of His) would likely produce simultaneous biventricular activation. For an intramyocardial placement, Thebesian vessels that drain right ventricular myocardial blood to the chamber of the right ventricle can be accessed using this delivery system.

Intracavitary lead placement would require transeptal puncture of the intraventricular septum with the use of a closure device appended to the lead. Such a closure device can have a similar coating to those of existing closure devices or arterial patches. A lead could be placed in the endocardial portion of the left ventricular free wall using this technique.

Uses for Pacing

For uses involving a pacemaker or biventricular pacing, a left ventricular lead delivered pericardially using a sheath of the invention might be preferential over coronary sinus delivery for the following reasons. First, a larger surface area of stimulation can be achieved using a left ventricular lead. Second, although the coronary veins demonstrate a large anastomotic network around the ventricle, certain portions of the ventricle have limited venous drainage from branches of the main coronary veins. Third, in certain locations, notably the mid-lateral and mid-posterior locations of the coronary venous vasculature, the epicardial portion of the veins has a large diameter. Therefore, a conventional pacing lead likely wedges into the perforating portion of these veins, and thus, stimulation may be occurring mid-myocardially rather than epicardially. Fourth, a sheath of the invention as described herein may be particularly applicable for simultaneous insertion of peizo electric crystals and transducers to measure contractility change. This may allow a one-step, single-access system to place leads at optimal sites and assess improvement with pacing both locally at a site and at a distance to the site.

A sheath of the invention also can be used for pacing with a combination of other subthreshold stimulation delivery systems.

Uses for Defibrillation

For uses involving defibrillators, a sheath of the invention may be particularly useful for selective deployment of defibrillator coils in an epicardial posterior/left ventricular location. The ability to place a wide area coil electrode in the posterior left ventricle just opposed to myocardial tissue in addition to an endocardially placed coil may significantly decrease the defibrillation threshold. Iterations that include rapid pacing of the right cardiac nerve (see below) may further decrease patient discomfort prior to the delivery of an otherwise painful shock.

Uses for Ablation

For uses involving ablation, epicardial pathways have continued to limit ablation success in some patients with, for example, Wolff-Parkinson-White syndrome. While pericardial approaches have been used for epicardial ablation, the removable nature of the handle in an apparatus of the invention and the fixity of screwed-in electrodes may allow for both mechanical and specific radiofrequency ablation targets.

In addition, the oblique sinus of the pericardial space is subjacent to potential pulmonary vein-to-pulmonary vein connections, either through the vena venarum or the vein of Marshall. This portion of the heart is highly mobile and would likely be technically demanding via existing pericardial approaches without a screw-in mechanism to map and ablate specifically.

Further, when epicardial pathways use the coronary venous system, fear of arterial damage has limited the ablation energy delivered. High-energy endocardial ablation, cryoablation, and pericardial ablation with standard catheter delivery systems are plagued by the inaccuracy of defining lesion size and limiting lesions to the venous system alone. With the steerable sheath described herein, an ablating lead can be screwed specifically into a vein of interest. Using traction, the vein can be moved from the neighboring artery and low energy lesions delivered to the venous wall alone.

Ablation for ventricular tachycardia is likely enhanced by existing pericardial approaches for ablation. However, this benefit may be enhanced even more if the ablating electrode could be fixed so as to allow more accurate endocardial manipulation of a catheter to an adjacent site to the fixed epicardial electrode. Radiofrequency or microwave energy could be delivered between these two electrodes to ensure transmural ablation.

Current attempts at radiofrequency ablation to promote neovascularization in patients with endstage ischemic heart disease have been met with minimal or no success. Part of the reason for this lack of or low success is the inability to perform multiple sequential procedures after accessing benefit. The deployable lead of the invention and the steerable sheath of the invention would allow epicardial revascularization with minimal invasiveness and also would allow lead shaft mobility and sequential fixation of the lead tip.

Other Uses

A steerable sheath of the invention and/or a deployable lead of the invention also can be used to treat coronary vasospasm. While the etiology of coronary vasospasm is largely dependent on humoral factors, a neural component is under investigation. If a significant neural component/tachycardia is found, the use of small fixed electrodes in the coronary vasculature may allow for modulation of the coronary arterial tone. This application may potentially benefit the closely related syndrome of inadequate coronary vasodilator reserve (syndrome X).

A steerable sheath or deployable lead of the invention also can be used in neuroregulation. While the autonomic and pain fiber innovation of the heart is quite wide spread, distinct clustering of these nervous tissues occurs insofar as to allow classification of cardiac nerves. The right cardiac nerve associated predominately with parasympathetic efferents and pain fiber afferents is located in the region of the medial superficial superior vena caval/RA junction. Pericardial access using any of the above-described delivery techniques can be used to gain access to the transverse sinus and through the transverse sinus to the aortocaval recess to allow placement of a lead. Devices capable of modulating the nervous system may allow cardiac modulation both for pain modification, heart rate, AV node modulation, and potential effects on arrhythmogenicity by modulating the autonomic tone. The left/posterior cardiac plexus would be readily accessible, particularly with transcoronary vein puncture techniques. Finally, the left anterior fat pad with parasympathetic afferent as well as efferent fibers can be accessed via the oblique sinus posterior to the left pulmonary veins.

A steerable sheath or deployable lead of the invention also can be used for phrenic stimulation. Patients with diaphragmatic paralysis from cervical trauma sometimes require operative placement of phrenic nerve stimulators. At times, repeat procedures are required in these patients to either change the lead or the lead location. Both the right and left phrenic nerves may be accessed through the pericardial space and using a steerable sheath of the invention, pericardial stimulators may be placed in a similar fashion to existing pacemakers.

A steerable sheath or deployable lead of the invention also can be used to treat neurocardiogenic syncope. One of the multitude of hypothesized factors precipitating neurocardiogenic syncope is unexplained great caval veins dilation. The suprasplenic vein, proximal hepatic vein, inferior vena cava, and superior vena cava are accessible through the pericardial reflections. Rapid pacing to increase venomotor tone can be effected using a steerable sheath of the invention. The manipulatable yet fixed nature of a steerable sheath of the invention also would be ideally suited for sustained/eluting delivery of cardiac and other genetic therapies and drug delivery systems. Epicardial pacing or cardiac contraction modulation impulses may be particularly helpful in treating neurocardiogenic syncope by increasing the force of contraction in addition to modifying autonomic function.

A deployable lead of the invention also can be used in patients that have congestive heart failure. An epicardially-placed deployable lead can be used as a pump to facilitate cardiac contraction. Additionally, deployment of multiple arms or multiple leads may help prevent cardiac mechanical dilation.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A deployable diagnostic or therapeutic implantable lead comprising a lead body having a longitudinal axis and at least one arm, said arm having a distal end and a hinged end, wherein, when said deployable lead is in a retracted position, said arm is adjacent to said longitudinal axis of said lead body and, when said deployable lead is in a deployed position, the distal end of said arm moves through an angle $\alpha$, wherein angle $\alpha$ is between about 0° and about 180° relative to said longitudinal axis of said lead body, said deployable lead further comprising a membranous material attached to said arm, wherein said arm comprises multiple electrodes.

2. The deployable lead of claim 1, wherein said electrodes are attached to said arms at said distal end of said arms.

3. The deployable lead of claim 1, wherein said electrodes are attached to said arms at a position medial to said distal end and said hinged end of said arm.

4. The deployable lead of claim 1, wherein the hinged end of the arms is attached to said lead body of said deployable diagnostic or therapeutic lead.

5. The deployable lead of claim 1, wherein said membranous material is further attached to a second arm.

6. The deployable lead of claim 1, wherein said membranous material is attached to said lead body of said deployable diagnostic or therapeutic lead.

7. The deployable lead of claim 1, wherein said membranous material is conductive.

8. The deployable lead of claim 1, wherein said membranous material further comprises electrodes.

9. The deployable lead of claim 1, wherein said angle α is between about 0° and about 90° relative to the longitudinal axis of said lead body.

10. The deployable lead of claim 1, wherein said angle α is between about 0° and about 180° relative to the longitudinal axis of said lead body.

* * * * *

UNITED STATES PATENT AND TRADEMARK OFFICE
CERTIFICATE OF CORRECTION

PATENT NO. : 7,620,458 B2
APPLICATION NO. : 11/075513
DATED : November 17, 2009
INVENTOR(S) : Friedman et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 614 days Delete the phrase "by 614 days" and insert -- by 1035 days --

Signed and Sealed this

Thirty-first Day of August, 2010

David J. Kappos
*Director of the United States Patent and Trademark Office*